US00PP37292P2

(12) United States Plant Patent
Guerrero

(10) Patent No.: US PP37,292 P2
(45) Date of Patent: Mar. 3, 2026

(54) ***ROSA* PLANT NAMED 'GEN R273'**

(50) Latin Name: *Rosa hybrida*
Varietal Denomination: GEN R273

(71) Applicant: GENVIV HOLDINGS, LLC, Miami, FL (US)

(72) Inventor: Maria Elena Guerrero, Quito (EC)

(73) Assignee: GENVIV HOLDINGS, LLC, Miami, FL (US)

( * ) Notice: Subject to any disclaimer, the term of this patent is extended or adjusted under 35 U.S.C. 154(b) by 0 days.

(21) Appl. No.: 19/310,785

(22) Filed: Aug. 26, 2025

(51) Int. Cl.
*A01H 5/02* (2018.01)

(52) U.S. Cl.
USPC ..... Plt./107

(58) Field of Classification Search
USPC ..... Plt./107
CPC ..... A01H 5/0222
See application file for complete search history.

*Primary Examiner* — Kent L Bell
(74) *Attorney, Agent, or Firm* — C. Anne Whealy

(57) ABSTRACT

A new and distinct cultivar of Rose plant named 'GEN R273', characterized by its upright and moderately strong flowering stems; moderately vigorous growth habit; dark green-colored leaves; purplish pink-colored flower petals and petaloids; and excellent postproduction longevity.

1 Drawing Sheet

Botanical designation: *Rosa hybrida.*
Cultivar denomination: 'GEN R273'.

CROSS-REFERENCED TO CLOSELY-RELATED APPLICATIONS

A European Community Plant Breeder's Rights application for the instant plant was filed by the Applicant/Assignee of the instant application, Genviv Holdings, LLC of Miami, Florida on Aug. 9, 2025, application number 2025/1777. Foreign priority is not claimed to this European Community Plant Breeder's Rights application.

BACKGROUND OF THE INVENTION

The present Invention relates to a new and distinct cultivar of Rose plant, botanically known as *Rosa hybrida*, commercially produced and used as a cut flower Rose plant, and hereinafter referred to by the name 'GEN R273'.

The new Rose plant is a product of a planned breeding program conducted by the Inventor in El Quinche, Pichincha, Ecuador. The objective of the breeding program was to develop new cut flower Rose varieties with unique flower colors and excellent postproduction longevity.

The new Rose plant originated from a cross-pollination made by the Inventor in March 2012 of a proprietary Rose selection identified as line R758, not patented, as the female, or seed, parent with a proprietary Rose selection identified as line R673, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in August 2013.

Asexual reproduction of the new Rose plant by bud grafting in El Quinche, Pichincha, Ecuador since February 2014 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'GEN R273'. These characteristics in combination distinguish 'GEN R273' as a new and distinct Rose plant:

1. Upright and moderately strong flowering stems.
2. Moderately vigorous growth habit.
3. Dark green-colored leaves.
4. Purplish pink-colored flower petals and petaloids.
5. Excellent postproduction longevity.

Plants of the new Rose differ from plants of the female parent selection in the following characteristics:

1. Plants of the new Rose have longer flowering stems than plants of the female parent selection.
2. Flowers of plants of the new Rose are larger with more petals per flower than flowers of plants of the female parent selection.
3. Flower petals of plants of the new Rose are purplish pink in color whereas flower petals of plants of the female parent selection are purple in color.

Plants of the new Rose differ from plants of the male parent selection in the following characteristics:

1. Stem thorns of plants of the new Rose are yellow green to pale yellow in color whereas stem thorns of plants of the male parent selection are brown in color.
2. Plants of the new Rose produce fewer flowers per spray than plants of the male parent selection.
3. Plants of the new Rose have more petals per flower than plants of the male parent selection.
4. Flower petals of plants of the new Rose are purplish pink in color whereas flower petals of plants of the male parent selection are red in color.

Plants of the new Rose can also be compared to plants of *Rosa hybrida* 'GEN R233', not patented. In side-by-side comparisons, plants of the new Rose differ from plants of 'GEN R233' in the following characteristics:

1. Stem thorns of plants of the new Rose are yellow green to pale yellow in color whereas stem thorns of plants of 'GEN R233' are reddish in color.
2. Plants of the new Rose have larger leaves than plants of 'GEN R233'.
3. Flowers of plants of the new Rose have more petals than flowers of plants of 'GEN R233'.
4. Flower petals of plants of the new Rose are darker purplish pink in color than flower petals of plants of 'GEN R233'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the upper left side of the photographic sheet is a side perspective view of a typical flowering spray of 'GEN R273'.

On the lower left side of the photographic sheet is a top perspective view of a typical flowering spray of 'GEN R273'.

At the upper right of the photographic sheet is a close-up view of a typical developed flower of 'GEN R273'.

And at the lower right of the photographic sheet are close-up views of the upper and lower surfaces of typical leaves of 'GEN R273'.

DETAILED BOTANICAL DESCRIPTION

The aforementioned photographic sheet and the following observations and measurements describe plants grown in ground beds in a polyethylene-covered greenhouse in Cayambe, Pichincha, Ecuador and produced under typical cut Rose production practices. Plants were grown year round and were 30 months old when the photographs and the description were taken. During the production of the plants, day temperatures ranged from 17° C. to 21° C., night temperatures ranged from 5° C. to 8° C. and light levels averaged 19,338 lux. In the following description, color references are made to The Royal Horticultural Society Colour Chart, 2015 Edition, except where general terms of ordinary dictionary significance are used.

Botanical classification: *Rosa hybrida* 'GEN R273'.

Parentage:

*Female, or seed, parent*.—Proprietary seedling selection of *Rosa hybrida* identified line R758, not patented.

*Male, or pollen, parent*.—Proprietary seedling selection of *Rosa hybrida* identified line R673, not patented.

Propagation:

*Type*.—By bud grafting.

*Time to initiate roots, summer*.—About seven to ten days at temperatures about 26° C. to 30° C.

*Time to produce a rooted young plant, summer*.—About 35 to 45 days at temperatures about 22° C. to 26° C.

*Root description*.—Medium in thickness, fibrous; typically close to 200A in color, actual color of the roots is dependent on substrate composition, water quality, fertilizers, substrate temperature and age of roots.

*Rooting habit*.—Moderately freely branching; dense.

Plant description:

*Plant and growth habit*.—Perennial shrub; upright and strong flowering stems; typically grown as a spray type cut rose; moderately vigorous growth habit and moderate growth rate.

*Productivity*.—Plants of the new Rose are highly productive with about 11.4 flowering stems developing per plant per year; typical cut flower stem length is 50 cm to 70 cm.

*Plant height*.—About 127.2 cm.

*Plant width* (*spread*).—About 29.2 cm.

*Lateral branches*.—Length: About 117.5 cm. Diameter: About 5.5 mm. Internode length: About 6.6 cm. Texture and luster: Smooth, glabrous; matte. Strength: Moderately strong. Color, developing: Close to 138B tinged with close to 166A. Color, developed: Close to 143A and 144A; at the internodes, close to 144B. Thorns: Density: About one to two thorns per linear centimeter. Height: About 3.4 mm. Length, at base: About 1 cm. Shape: Deltoid; slightly incurved with sharp acute apices. Color, immature: Close to 144A. Color, mature: Close to 160A.

Leaf description:

*Arrangement*.—Alternate; compound with typically five to seven leaflets per leaf.

*Leaf length*.—About 14.3 cm.

*Leaf width*.—About 9 cm.

*Leaflet length*.—About 4.1 cm.

*Leaflet width*.—About 2.8 cm.

*Leaflet shape*.—Ovate.

*Leaflet apex*.—Acuminate.

*Leaflet base*.—Obtuse.

*Leaflet margin*.—Serrate.

*Leaflet texture and luster, upper surface*.—Smooth, glabrous; semi- glossy.

*Leaflet texture and luster, lower surface*.—Smooth, glabrous; matte.

*Leaflet venation pattern*.—Pinnate and arcuate.

*Leaflet color*.—Developing leaflets, upper surface: Close to 147A tinged with close to 187A. Developing leaflets, lower surface: Close to 146A. Fully expanded leaflets, upper surface: Close to 147A; venation, close to 145A. Fully expanded leaflets, lower surface: Close to 138B; venation, close to 145A.

*Petioles*.—Length: About 4.2 cm. Diameter: About 1.3 mm. Strength: Moderately strong. Texture and luster, upper surface: Slightly hirsutulous; matte. Texture and luster, lower surface: Smooth, glabrous; semi-glossy. Color, upper surface: Close to 147A. Color, lower surface: Close to 138B.

*Stipules*.—Arrangement and appearance: Two, adnate to the petiole, scale-like in appearance with acute apices and tapering towards the base; margins, ciliolate. Length: About 2.9 cm. Width: About 3.6 mm. Texture and luster, upper and lower surfaces: Smooth, glabrous; membranous; matte. Venation pattern: Pinnate and arcuate. Color, upper surface: Close to 147A. Color, lower surface: Close to 138B.

Flower description:

*Flower type and arrangement*.—Symmetrical rosette flowers; flowers typically grown as spray types with about five to six flowers developing per flowering stem; flowers face upright.

*Flowering season*.—Plants of the new Rose flower year-round under greenhouse conditions in Ecuador; plants begin flowering about 100 days after planting young plants.

*Spray diameter*.—About 19.2 cm.

*Spray height*.—About 24.3 cm.

*Flower diameter*.—About 5.8 cm.

*Flower depth* (*height*).—About 3 cm.

*Flower longevity*.—Excellent postproduction longevity; flowers maintain good substance for about 41 days on the plant and as a cut flower, about two weeks; flowers persistent.

*Fragrance*.—None detected.

*Flower buds*.—Length: About 2.1 cm. Diameter: About 3.8 cm. Shape: Ovoid. Texture and luster: Smooth, glabrous; matte. Color: Close to 68C.

*Petals*.—Quantity: About 30 per flower arranged in about five whorls; petals imbricate, but not fused. Length: About 2.9 cm. Width: About 3 cm. Shape: Roughly orbicular. Apex: Rounded. Base: Cuneate to rounded. Margin: Entire; slightly undulate. Texture and luster, upper and lower surfaces: Smooth, glabrous; matte. Color: When opening, upper surface: Close to 65B. When opening, lower surface: Close to 65A. Fully opened, upper surface: Close to 63D; venation, close to 154B; color becoming closer to 75C with subsequent development. Fully opened, lower surface: Close to 68C; venation, close to 154B; color becoming closer to 75C with subsequent development.

*Petaloids*.—Quantity: About six in a single whorl; size and shape are variable. Length: About 2.3 cm. Width: About 1.8 cm. Texture and luster, upper and lower surfaces: Somewhat rugose, glabrous; matte. Color: When opening, upper and lower surfaces: Close to 65A. Fully opened, upper and lower surfaces: Close to 68C; venation, close to 154B; color becoming closer to 77C with subsequent development.

*Sepals*.—Quantity per flower: Typically five in a single whorl. Length: About 2.7 cm. Width: About 1 cm. Shape: Lanceolate. Apex: Acuminate. Base: Truncate. Margin: Entire; ciliate and ciliolate. Texture and luster, upper surface: Glandular; matte. Texture and luster, lower surface: Hirsutulous; matte. Color: When opening, upper surface: Close to 144A. When opening, lower surface: Close to 144B. Fully opened, upper surface: Close to 144A. Fully opened, lower surface: Close to 144C.

*Pedicels*.—Length: About 5.2 cm. Diameter: About 2.4 mm. Strength: Moderately strong. Aspect: About 45° from the flowering stem axis. Texture and luster: Glandular and hispid; semi-glossy. Color: Close to 143C.

*Reproductive organs*.—Stamens: Quantity: About 94 per flower. Filament length: About 7 mm. Filament color: Close to 2B. Anther size: About 2.1 mm by 3.3 mm. Anther shape: Reniform. Anther color: Close to 2C. Pollen amount: Moderate. Pollen color: Close to 22B. Pistils: Quantity: About 80 per flower. Pistil length: About 8.7 mm. Stigma diameter: About 0.5 mm. Stigma shape: Lobed. Stigma color: Close to 1C. Style length: About 8.7 mm. Style color: Close to 2D. Ovary color: Close to 145C. Receptacle height: About 8.5 mm. Receptacle diameter: About 7.8 mm. Receptacle shape: Cup-shaped. Receptacle texture: Smooth, glabrous. Receptacle color: Close to 144A. Fruits and seeds: To date, fruit and seed development have not been observed on plants of the new Rose.

Pathogen & pest tolerance: To date, plants of the new Rose have not been observed to be tolerant to pathogens and pests common to Rose plants.

It is claimed:

1. A new and distinct Rose plant named 'GEN R273' as herein illustrated and described.

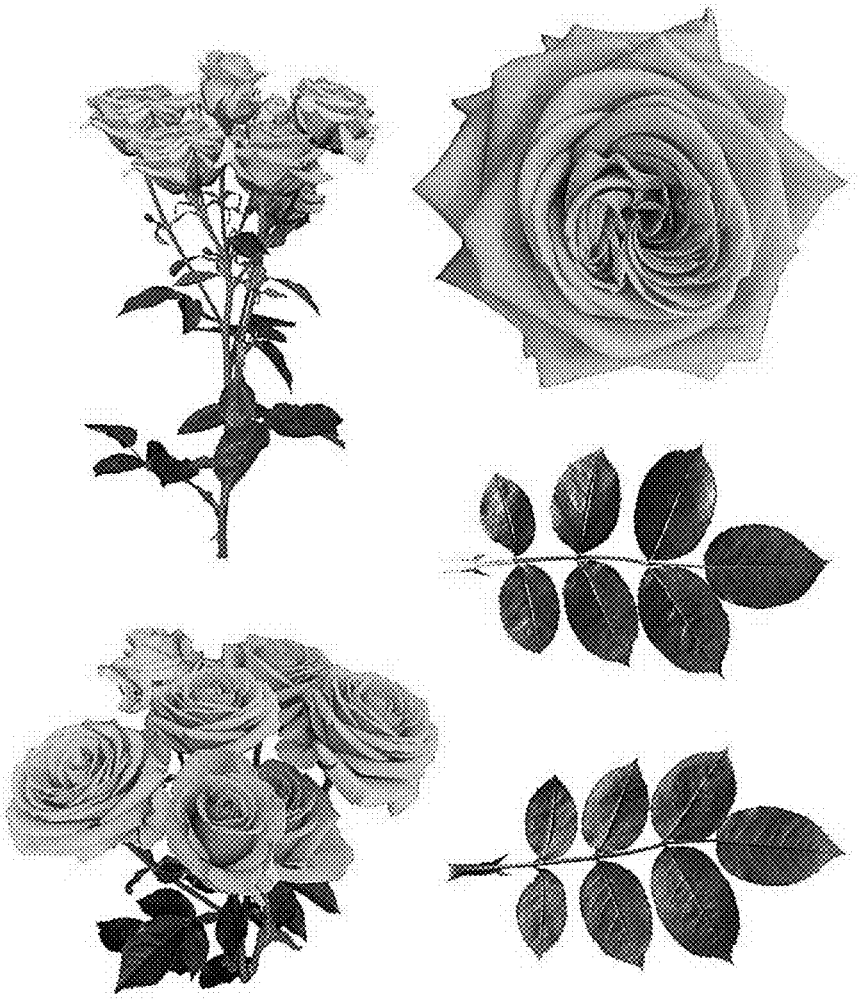

* * * * *